(12) United States Patent
Kapadia et al.

(10) Patent No.: US 6,703,525 B2
(45) Date of Patent: Mar. 9, 2004

(54) SULFONAMIDE INTERMEDIATES AND METHODS OF PRODUCING SAME

(75) Inventors: Suresh R. Kapadia, Danbury, CT (US); Jinhua J. Song, Hopewell Junction, NY (US); Nathan K. Yee, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/264,689

(22) Filed: Oct. 4, 2002

(65) Prior Publication Data

US 2003/0065034 A1 Apr. 3, 2003

Related U.S. Application Data

(63) Continuation-in-part of application No. 09/834,797, filed on Apr. 13, 2002, now Pat. No. 6,608,052, which is a continuation-in-part of application No. 09/505,582, filed on Feb. 16, 2000, now Pat. No. 6,358,945.

(51) Int. Cl.⁷ .................... C07C 303/38; C07C 209/36
(52) U.S. Cl. .................... 564/92; 564/99; 564/420; 564/422; 564/423
(58) Field of Search .................... 564/92, 99, 420, 564/422, 423

(56) References Cited

U.S. PATENT DOCUMENTS 6,608,052 B2 * 8/2003 Breitfelder et al. ...... 514/227.8

OTHER PUBLICATIONS

Entwistle et al., Chem. Soc., Perkin trans, 1, 1975, 1300.*

\* cited by examiner

*Primary Examiner*—Richard L. Raymond
(74) *Attorney, Agent, or Firm*—Robert P. Raymond; Anthony P. Bottino; Timothy X. Witkowski

(57) ABSTRACT

Disclosed are intermediates of the formula (A) and methods of making same. The intermediate compounds are useful in the synthesis of heteroaryl/aryl urea compounds,

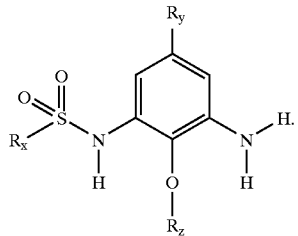

(A)

4 Claims, No Drawings

SULFONAMIDE INTERMEDIATES AND METHODS OF PRODUCING SAME

APPLICATION DATA

This application is a continuation-in-part of U.S. patent application Ser. No. 09/834,797 filed Apr. 13, 2002, now U.S. Pat. No 6,608,052, which is a continuation-in-part of U.S. patent application Ser. No. 09/505,582 filed Feb. 16, 2000 now U.S Pat. No. 6,358,945.

TECHNICAL FIELD OF THE INVENTION

This invention relates to sulfonamide intermediate compounds and processes of making same. The compounds are useful for synthesis of compounds which inhibit production of cytokines involved in inflammatory processes.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis.

U.S. Pat. No. 6,358,945 and U.S. application Ser. No. 09/834,797, now U.S. Pat. No. 6,608,052, describe heteroaryl urea compounds useful for treating cytokine mediated diseases. One of the general schemes for producing such compounds is found in Scheme I of U.S. Ser. No. 09/834,797:

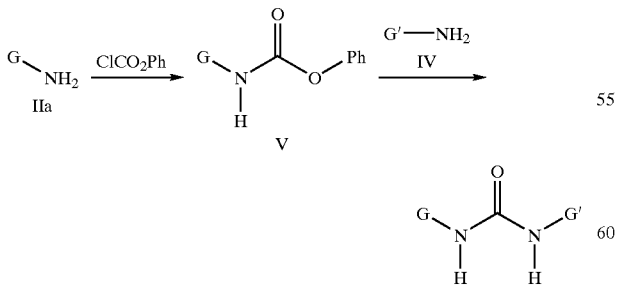

G' = Ar—X—Y—Z or a precursor of I.

One of the formula IIa arylamine intermediates is a sulfonamide of the formula:

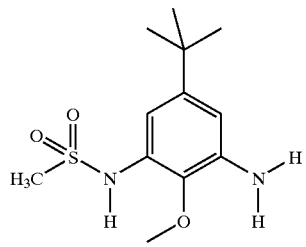

5-tert-Butyl-3-methanesulfonamido-2-methoxyaniline.

Example 2 disclosed therein describes its synthesis, however the three step synthesis provides a less than desirable approximate 70% yield,

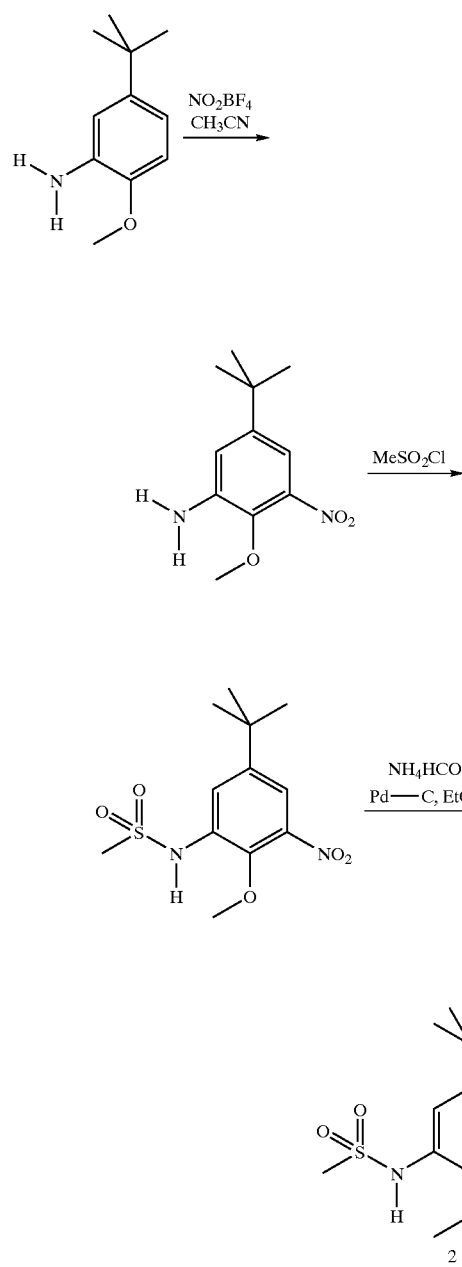

Example 1 in the application demonstrates another route to obtain the reduced amine in step 1 above:

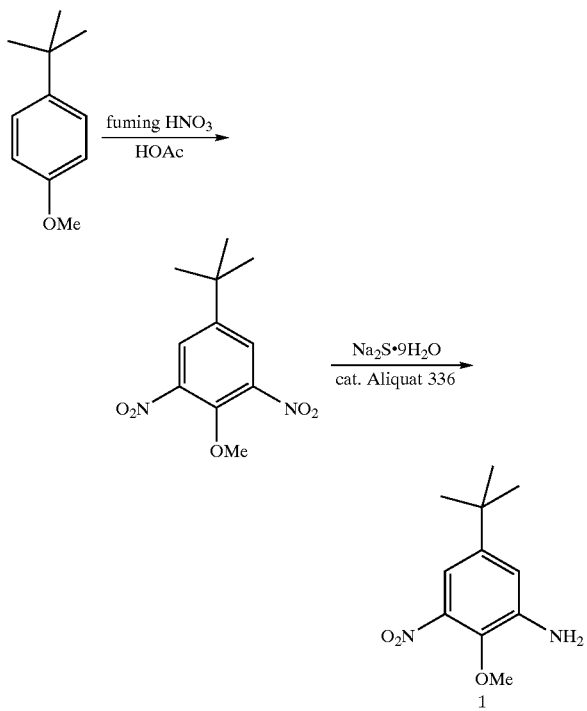

Selective reduction of one nitro group in dinitroaryl compounds has been shown by Entwistle, et al. using cyclohexene for the transfer hydrogenation. Entwistle, I. D. et al. *J. Chem. Soc., Perkin trans,* 1, 1975, 1300. During this process benzene is formed as a byproduct which is a known carcinogen.

The present application provides an improved more economical process for synthesis of such intermediates by an increasing overall yield to approximately 81% and producing toluene rather than benzene, toluene being more environmentally safe.

BRIEF SUMMARY OF THE INVENTION

It is an object of the invention to provide an improved sythesis for compounds of the formula (A):

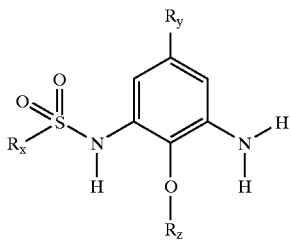

(A), such as 5-tert-Butyl-3-methanesulfonamido-2-methoxyaniline.

DETAILED DESCRIPTION OF THE INVENTION

All terms as used herein in this specification, unless otherwise stated, shall be understood in their ordinary meaning as known in the art.

The term "carbocycle" shall be understood to mean an aryl or an aliphatic hydrocarbon radical containing from three to twelve carbon atoms. Carbocycles include hydrocarbon rings containing from three to ten carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably. All carbocycles are optionally substituted.

The term "aryl" as used herein shall be understood to mean aromatic carbocycle as defined herein. Each aryl unless otherwise specified includes it's partially or fully hydrogenated derivative. For example, naphthyl may include it's hydrogenated derivatives such as tetrahydranaphthyl. Other partially or fully hydrogenated derivatives of the aryl compounds described herein will be apparent to one of ordinary skill in the art.

All akyl groups shall be understood to be C1–10 and branched or unbranched, and optionally substituted where appropriate.

The term "halogen" as used in the present specification shall be understood to mean bromine, chlorine, fluorine or iodine.

The term 'optionally substituted' shall be understood to mean one or more substitutions such as alkyl, alkoxy, acyl, carbocycle, amino, amido, hydroxy, carboxy, and the like.

MTBE—methyl t-butyl ether
DMF—N,N-dimethylformamide;
THF—tetrahydrofuran;
RT or rt—room temperature.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

In a generic aspect of the invention, there is provided a process of producing compounds of the formula

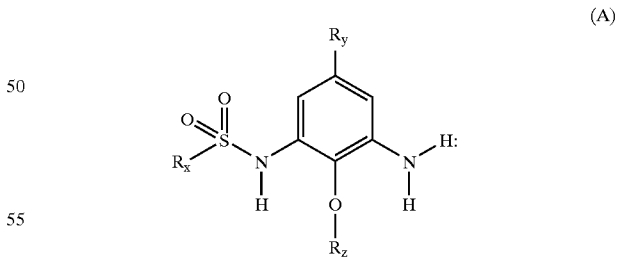

(A)

wherein $R_x$ and $R_z$ are each independently chosen from C1–10 alkyl or carbocycle; preferably, $R_x$ and $R_z$ are C1–10 alkyl, more preferably C1–5 alkyl, most preferably methyl;

$R_y$ is chosen from C1–10 alkyl, preferably C1–5 alkyl and more preferably tert-butyl;

said method comprising:

Step 1

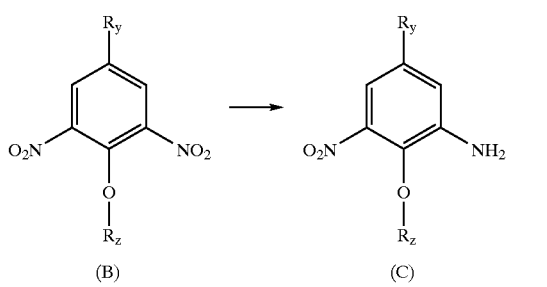

reducing a dinitroaryl compound (B) using a suitable reducing agent such as hydrogen with Pd/C (palladium over carbon) as a catalyst, in the presence of a methyl cyclohexene such as 4-methyl-1-cyclohexene or 3-methyl-1-cyclohexene, and further in the presence of a suitable solvent, such as THF, an alcohol, for example ethanol, methanol and isopropyl alcohol (IPA), to produce intermediate (C);

Step 2

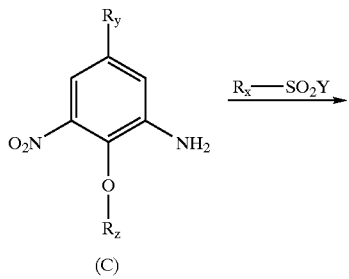

reacting the product of step 1 (C) with an alkyl or aryl sulfonyl halide $R_x$—$SO_2$—Y wherein $R_x$ is as defined above and Y is a halogen, preferably Cl, in the presence of an amine base such as triethylamine, diisopropylethyl amine and pyridine, preferably pyridine, and an aprotic solvent such as toluene, MTBE, dichloromethane, THF and ether, preferably toluene, to produce intermediate (D);

Step 3

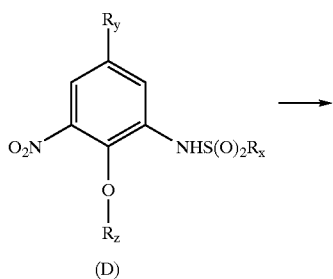

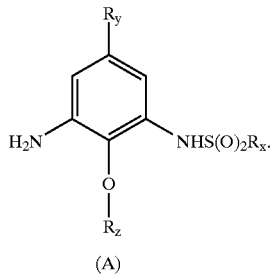

Step 3, the reduction of nitro in (D) to amino can be carried out with a suitable reducing agent such as $H_2$, preferable at 50 psi using Pd/C as catalyst. This reaction can also be carried out using transfer hydrogenation condition e.g. ammonium formate, formic acid, hydrazine, phosphinic acid, sodium phosphinate, etc.

Suitable reaction times and temperatures will be apparent to those skilled in the art, preferred are those found in the working example below.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

N-(3-Amino-5-tert-butyl-2-methoxy-phenyl)-methanesulfonamide

Step 1

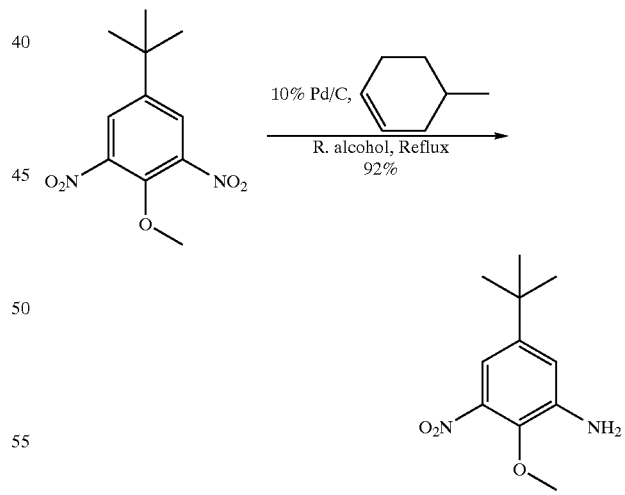

To a stirring solution of dinitro compound (1.10 Kg, 4.32 mole) in reagent alcohol (8.25 L) was added 10% Pd/C (50% $H_2O$, 55.00 g) and the reaction mixture heated to 78–79° C. (internal temp.). 4-Methyl-1-cyclohexene (0.52 L, 1.0 eq.) was added to the refluxing reaction mixture over 70 minutes (only ~10 ml in the beginning, stir for 10 min and then add the rest slowly). Reaction mixture was refluxed for 3 h. (HPLC). $2^{nd}$ installment of 4-methyl-1-cyclohexene (0.26 L) was added over ~30 min. After refluxing for 3 h (HPLC), 3rd installment of 4-methyl-1-cyclohexene (0.27 L) was added over 0.5 h and refluxing continued until all starting material was consumed (~5 h) as indicated by HPLC (product-94%, sm-0.4% and diamine 4.6%). Heating mantle was removed and the reaction mixture was stirred at room temperature overnight.

Catalyst was filtered and filtrate was concentrated until molar ratio of ethanol to the product was ~5:1 (NMR). 2N HCl (220.0 ml) was added slowly such that reaction temperature did not exceed 20° C. Reaction mixture was then diluted with water (5.50 L). Yellow crystals crashed out. After stirring for 1 h, product was filtered, washed thoroughly with water and dried under the flow of $N_2$. Yield: 0.902 Kg, 93%. Structure was confirmed by NMR.

Step 2

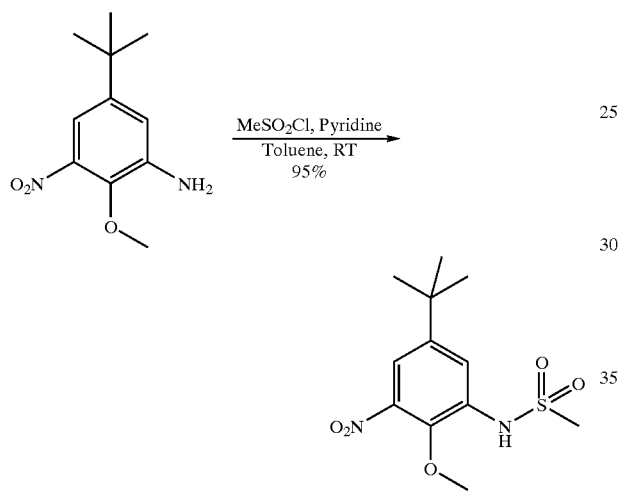

Dry pyridine (0.902 L) was added to a stirring solution of nitroaniline (902 g, 4.03 mole) in dry toluene (3.62 L) at room temperature. After stirring for 15 min, methanesulfonyl chloride (342 ml, 4.42 mole, 1.10 eq) was added to the reaction mixture over 80 min. Internal temperature was allowed to rise up to 33–35° C. (water bath cooling if necessary). After completion of the addition, cooling was removed and reaction mixture was stirred at ambient temperature for 16 h. (HPLC 98.4% product, 0.29% sm and 0.82% bis-sulfonamide).

Maintaining the reaction temperature <20° C., reaction mixture was quenched with water (3.62 L) followed by addition of 2N HCl (3.62 L), again keeping internal temperature >20° C. It was stirred vigorously for 15 min and layers were separated. Aq layer was discarded and organic phase was washed with 2.5% aq. NaCl solution (3.62 L). Heptane (7.24 L) was added slowly to the stirring organic phase when product crystallized out. After stirring for 0.5 h at room temperature and 0.5 h at 2° C., product was filtered, washed with heptane and dried under reduced pressure to give light yellow crystalline material. yield: 1.16 Kg (95.4%). Purity: 99.6%.

Step 3

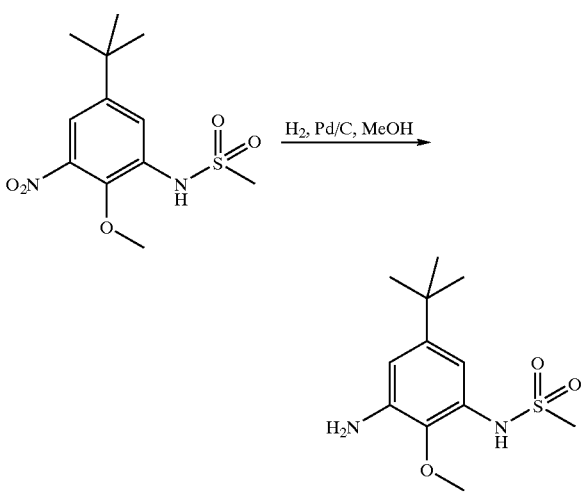

To a solution of nitro sulfonamide (10.0 g, 33.07 mmole) in methanol (80 ml) in a parr bottle was added 10% Pd/C (50% water, 160 mg) and the mixture was subjected to hydrogenation at 50 psi of $H_2$ for 18 h. HPLC showed a complete conversion. THF (15 ml) was added to the reaction mixture to dissolve precipitated product. Catalyst was filtered. Filtrate was evaporated to dryness. Residue was dissolved in THF (23 ml) followed by slow addition of heptane when product crystallized out. It was stirred for an hour, filtered and dried. Yield: 8.35 g, 92%%. Purity: >99.6%. Structure was confirmed by NMR.

What is claimed is:

1. A process of producing compounds of the formula (A):

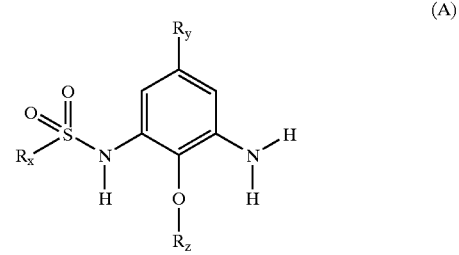

(A)

wherein
$R_x$ and $R_z$ are each independently chosen from C1–10 alkyl or carbocycle;
$R_y$ is C1–10 alkyl;
said method comprising:
Step 1

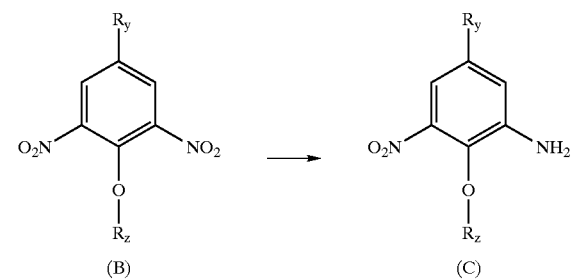

at a suitable temperature and suitabale reaction time, reducing a dinitroaryl compound (B) using a suitable reducing agent and a catalyst, in the presence of methyl cyclohexene, and further in the presence of a suitable solvent, to produce intermediate (C);
Step 2

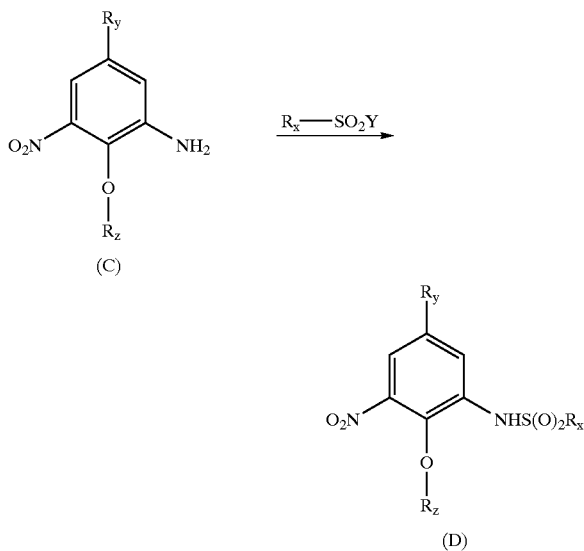

(C)

(D)

at a suitable temperature and suitable reaction time reacting the product of step 1 (C) with an alkyl or aryl sulfonyl halide $R_x$—$SO_2$—Y wherein $R_x$ is as defined above and Y is a halogen, in the presence of an amine base and an aprotic solvent to produce intermediate (D);
Step 3

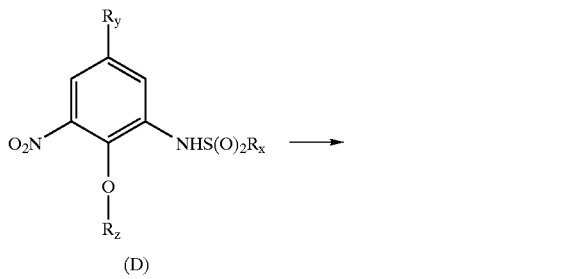

(D)

-continued

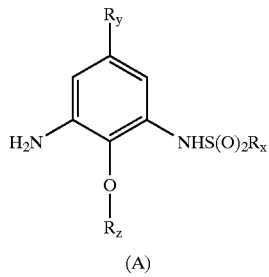

(A)

at a suitable temperature and suitabale reaction time, reducing under suitable conditions of nitro in (D) to amino with a suitable reducing agent using a catalyst, to produce a compound of the formula (A).

2. The process according to claim 1 and wherein $R_x$ is C1–10 alkyl;

$R_y$ C1–5 alkyl;

In Step 1 the reducing agent is hydrogen with Pd/C in the presence of 4-methyl-1-cyclohexene or 3-methyl-1-cyclohexene, and further in the presence of a solvent chosen from THF, ethanol, methanol and isopropyl alcohol (IPA), In Step 2, Y is Cl, the amine base is chosen from triethylamine, diisopropylethyl amine and pyridine, the aprotic solvent is chosen from toluene, MTBE, dichloromethane, THF and ether;

In Step 3, the reducing agent is $H_2$, at 50 psi using Pd/C as catalyst, the transfer hydrogenation condition is with a reagant chosen from ammonium formate, formic acid, hydrazine, phosphinic acid and sodium phosphinate.

3. The process according to claim 2 and wherein $R_x$ is C1–5 alkyl;

$R_y$ is tert-butyl;

in Step 2 the amine base is pyridine, the aprotic solvent is toluene.

4. The process according to claim 3 and wherein $R_x$ is methyl and $R_z$ is methyl.

* * * * *